United States Patent [19]

Pâques et al.

[11] Patent Number: 5,068,106

[45] Date of Patent: Nov. 26, 1991

[54] T-PA SOLUTION OF HIGH CONCENTRATION AND USE OF THE SOLUTION IN HUMAN AND VETERINARY MEDICINE

[75] Inventors: Eric P. Pâques, Marburg; Hans-Arnold Stöhr, Wetter, both of Fed. Rep. of Germany

[73] Assignee: Behringwerke Aktiengesellschaft, Marburg, Fed. Rep. of Germany

[21] Appl. No.: 201,880

[22] Filed: Jun. 3, 1988

[30] Foreign Application Priority Data

Jun. 5, 1987 [DE] Fed. Rep. of Germany ......... 371889

[51] Int. Cl.$^5$ .................. A61K 37/547; A61K 37/54; C12N 9/64; C12N 9/72
[52] U.S. Cl. .................. 424/94.3; 424/94.63; 424/94.64; 435/212; 435/215; 435/236
[58] Field of Search ............... 424/94.63, 94.64, 94.3; 435/212, 215, 236

[56] References Cited

U.S. PATENT DOCUMENTS

| | | | |
|---|---|---|---|
| 4,258,030 | 3/1981 | Sasaki et al. | 424/94.63 |
| 4,440,679 | 4/1984 | Fernandes et al. | 424/101 |
| 4,568,544 | 2/1986 | Hasegawa et al. | 424/94.64 |

FOREIGN PATENT DOCUMENTS 156169 10/1985 European Pat. Off. .
217379 4/1987 European Pat. Off. .
0218112 4/1987 European Pat. Off. .

OTHER PUBLICATIONS

Ranby et al, Progress in Fibrinolysis, vol. 5 (1981), pp. 233-235.

*Primary Examiner*—Jacqueline Stone
*Attorney, Agent, or Firm*—Finnegan, Henderson, Farabow, Garrett and Dunner

[57] ABSTRACT

In the preparation of parenteral solutions for the therapy and prophylaxis of thromboses and embolisms, because of the poor solubility of t-PA hitherto either the infusion of very large volumes has been necessary, or else a solution with a low volume and a high t-PA concentration has been prepared at the expense of setting up a non-physiologically low pH of 2 to 5.

Hence, the present invention relates to a process for the preparation of a solution of high concentration of a protein having plasminogen activator activity, where an increase in stability and solubility is achieved by adding at least two substances from the group of D- and/or L-amino acids, their salts, derivatives or homologs. This invention also relates to a process for the pasteurization of a protein solution having t-PA activity, and to a t-PA-containing solution prepared by the claimed process, and to the use of this solution as a fibrinolytic in human and veterinary medicine.

13 Claims, No Drawings

T-PA SOLUTION OF HIGH CONCENTRATION AND USE OF THE SOLUTION IN HUMAN AND VETERINARY MEDICINE

The invention relates to a process for the preparation of a solution of high concentration of a protein having plasminogen activator activity, to a solution prepared by the claimed process, and to the use of this solution in human and veterinary medicine.

The body has two systems, which are in equilibrium, in order to protect itself from blood loss and from thromboses: the coagulation system and the fibrinolytic system. The interplay between the two ensures that insoluble fibrin polymers are initially produced to stop bleeding and are then degraded during wound healing by the lytic process of fibrinolysis.

Thrombin and plasmin are the key enzymes in both systems. Under physiological conditions, the dynamic equilibrium between the coagulation and fibrinolysis systems is under the control of the thromboplastic activity of thrombin and of the thrombolytic activity of plasmin. The relevant inhibitors contribute to the equilibrium. A predominance of one of the two systems may have fatal consequences, namely not only hemorrhages and thromboses but also vascular damage.

Plasmin, which has thrombolytic activity, is a relatively non-specific, trypsin-like serine protease. It is synthesized in the form of an inactive precursor, plasminogen. Plasminogen circulates as inactive precursor in the blood and is activated only in response to particular stimuli. The conversion of plasminogen into plasmin is catalysed by plasminogen activators.

Plasminogen can be activated by four different plasminogen activator systems:
1. a factor XII-dependent system,
2. a plasminogen activator isolated from Streptococci, streptokinase,
3. tissue plasminogen activator (t-PA) and
4. urinary plasminogen activator (u-PA or urokinase).

Activation via the factor XII-dependent system has only minor physiological importance. Although the bacterial plasminogen activator streptokinase remains of great therapeutic importance, it has the disadvantage, in the same way as the urinary plasminogen activator urokinase, that after its administration or release it is active in the entire vascular system, i.e. results in activation of plasminogen not only at the target site. Finally, tissue plasminogen activator is a protein which is present in many tissues and tissue fluids, and it displays its full fibrinolytic activity only after binding to fibrin. Thus, plasminogen activation by t-PA is a reaction which takes place specifically only at the target site and is not associated with the risk of simultaneous non-specific proteolysis of other plasma proteins.

Hypofunction of the fibrinolytic system, irrespective of the cause, may result in vascular occlusions due to thrombus formation. Examples of the consequences of such thrombi are myocardial infarcts, pulmonary embolisms or strokes. Administration of plasminogen activators plays a significant part in the prophylaxis and therapy of many disorders deriving from hypofunction of the fibrinolytic system. Ideally, the administered plasminogen activator should allow fibrin-specific lysis therapy which is free of side effects. This requirement can be met only by tPA, since t-PA activation, as already mentioned, depends on binding to fibrin. It is possible to produce t-PA from animal cells in amounts sufficient for therapy. However, t-PA has, exactly as has urokinase, a half-life of only 3 to 8 minutes in the human body. The consequence of this is that a constant and continuous t-PA delivery must be made possible, for example in the form of an intravascular infusion. At the same time, the volume of the amount of fluid which is delivered must be kept as small as possible in order not additionally to stress patients with cardiac or renal insufficiency. Hence the highest possible concentration must be a requirement for the formulation of physiologically tolerated parenteral solutions containing t-PA.

t-PA concentrations of 3,000 to 50,000 U/ml can be reached by addition of lysine or ornithine under the conditions described in EP-A 156,169. This would result, at the therapeutic dosage required, in delivery of a very large amount of liquid. Addition of lysine or ornithine as described in European Patent Application EP 156,169 cannot result in solutions containing t-PA which can be reasonably used therapeutically.

German Offenlegungsschrift 3,617,753 describes t-PA solutions in which t-PA concentrations of up to 5,000,000 U/ml are reached by lowering the pH to 2 to 5. Although this achieves a therapeutically reasonable t-PA concentration in the solution, it is also at the expense of infusion of a solution with a grossly non-physiological pH. Administration of such solutions results unavoidably in skin irritation and vascular damage in the neighborhood of the infusion site.

Hence the object of the present invention was to provide a process which allows the preparation of highly concentrated, physiologically tolerated solutions, which can be administered parenterally, of a protein having t-PA activity.

This object is achieved according to the invention by adding to the solution at least two substances from the group of D- and/or L-amino acids, their salts, derivatives or homologs.

It has emerged, surprisingly, that addition of at least two substances from the group of D- and/or L-amino acids, their salts, derivatives or homologs has a stability-promoting effect on proteins having t-PA activity. At the same time, an increased solubility of the protein can be observed by combination of several of these substances. The extent of both effects is completely unexpected. Both the increase in stability and the rise in the solubility are apparently derived from a synergism of the individual actions.

The substances according to the invention, for example lysine, ornithine, arginine, diaminopimelic acid, agmatine, creatine, guanidinoacetic acid, acetylornithine, citrulline, argininosuccinic acid, tranexamic acid and c-aminocaproic acid, are outstandingly suitable for the formulation of solutions intended for infusion. A feature which is common to them all is the presence of a basic group in the form of an amino and/or a guanidino group.

A combination of arginine and lysine, preferably 0.001 to 1 mol/l, particularly preferably 0.01 to 0.5 mol/l, has proved particularly suitable for the preparation of a solution of high concentration of a protein having plasminogen activator activity. Thus, for example, it has been shown that the t-PA activity in a cell culture supernatant had fallen to 31% of the initial value after incubation at +4° C. for 5 days, whereas addition of 0.1 mol/l arginine and 0.1 mol/l lysine to a parallel sample resulted in a decrease in activity of only 5% after the same incubation time.

The stability-promoting and solubility-increasing effect of the substances according to the invention has been observed both for tissue plasminogen activator in its one-or two-chain form and for derivatives which occur naturally or have been prepared by synthesis or genetic manipulation, or for combinations of t-PA and one of its derivatives which occurs naturally or has been prepared by synthesis or genetic manipulation, and/or pro-urokinase or urokinase.

The isolation of the t-PA or of a protein having the same activity can be carried out by customary methods. Where appropriate, the protein having t-PA activity is first dissolved by dialysis against a buffered solution of a chaotropic agent, for example KSCN, concentrated in this state to the desired t-PA concentration, and then dialyzed against a buffered solution containing at least two of the substances according to the invention, preferably arginine and lysine. For example, this will entail the solution of a protein having plasminogen activator activity being dialyzed first against approximately 1.6 mol/l KSCN in approximately 0.05 mol/l tris-HCl, pH 7, and then against arginine and lysine, each 0.1 mol/l, in 0.05 mol/l tris-HCl, pH 7.

However, it is likewise possible to achieve the stabilitypromoting effects by direct addition of the substances according to the invention to the supernatant of a cell culture. The supernatants of cell cultures treated according to the invention result in the isolation of proteins which have t-PA activity and whose specific activity is triple that of control solutions.

The stability- and solubility-promoting effects of the substances according to the invention are independent of pH over a wide range. The pH of the corresponding proteincontaining solution can be between 5 and 10 and is preferably 6 to 8.

It is customary for solutions intended for parenteral administration to be sterilized by filtration because many of the biologically active molecules would be decomposed by pasteurization. However, the presence of viruses can never be completely ruled out in products sterilized by filtration, as is demonstrated by the SV 40 contamination of smallpox vaccine or the transmission of the AIDS virus by factor VIII preparations. A considerable advantage of the process which is described here is that the proteins having t-PA activity are sufficiently stabilized by the addition of substances according to the invention that their activity is substantially retained even after pasteurization. Whereas a buffered t-PA-containing solution had, for example, after a low-temperature pasteurization, retained only 0.5 per cent of the initial activity, it was possible to retain about 85 per cent of the initial activity by addition of arginine and lysine, 1 mol/l each.

The stabilizing effect of the substances according to the invention is substantially independent of the type of pasteurization. Thus, the pasteurization can be carried out at pH 5 to 10 by incubation at temperatures between 40° C. and 90° C. for 1 to 60 hours.

However, the pasteurization is expediently carried out at virtually physiological pH, i.e. between pH 6 and pH 8, by incubation at temperatures between 50° C. and 70° C. for 6 to 16 hours.

The most preferred embodiment is a low-temperature pasteurization at approximately pH 7, i.e. the protein having t-PA activity being incubated at 60° C. for 10 hours.

The protein-containing solution can, where appropriate, be mixed with further additives, for example mono- or disaccharides, sugar alcohols and, where appropriate, other additional components such as, for example, albumins, gelatin, Haemaccel, sodium chloride, calcium chloride, heparin, EDTA, glycine or detergents. These additional components are added in physiologically tolerated amounts for the purpose of, for example, stabilization, buffering of the system, inhibition of proteases, reducing the surface tension and regulating the osmolarity.

Addition of sucrose or sorbitol has a further stability-promoting effect during the pasteurization. Thus, the content of active molecules remaining after pasteurization in a glycine-buffered t-PA solution which contains arginine and lysine, 0.5 mol/l each, can be increased from about 81 per cent to 96 per cent. In this connection, addition of 0.2 to 2 kg of sucrose or sorbitol per liter is preferred.

The activity of t-PA, or proteins having the same action, which have been treated according to the present invention, is retained even after freeze-drying followed by dissolution in sterilized water immediately before use.

It is possible to prepare, by the process according to the invention, a protein solution which has t-PA activity and whose concentration is more than $5 \times 10^6$ U/ml. This concentration ensures problem-free administration even on continuous infusion over a prolonged period. It is possible in patients with extreme difficulties with excretion to raise the t-PA concentration to $30 \times 10^6$ U/ml without problems of solubility or stability occurring.

It has emerged, irrespective of the chosen t-PA concentration, that the activity of solutions prepared according to the invention is essentially retained after pasteurization. The aqueous protein solution having t-PA activity according to the invention is the first plasminogen activator preparation which is sterilized by pasteurization and has a therapeutically worthwhile specific activity concentration.

The solution according to the invention is equally suitable for use in human and in veterinary medicine. Since only physiologically tolerated substances are added, neither inflammations nor skin irritation or vascular damage occur on administration of the solution according to the invention.

The preferred uses of the solution according to the invention are the therapy and prophylaxis of thromboses and embolisms, i.e. the preparation according to the invention can be used as a fibrinolytic.

The examples illustrate the invention.

EXAMPLE 1 t-PA-producing CHO cells (Chinese hamster ovary) were cultured in 20 liters of Dulbecco's modified Eagle's medium containing 5% bovine serum. The cell culture supernatants were harvested every 24 h and replaced by fresh medium.

The cell culture supernatants harvested under sterile conditions were stored at +4° C. for 5 days in the presence or absence of 0.1 mol/l arginine and 0.1 mol/l lysine.

The t-PA activity was determined each day by the method of Ranby (Progress in Fibrinolysis 5, 233–235, 1981).

| Duration of incubation at 4° C. (days) | Activity in % | |
|---|---|---|
| | Cell culture supernatant without Arg, Lys | Cell culture supernatant 0.1 mol/l Arg + 0.1 mol/l Lys |
| — | 100 | 100 |
| 1 | 65 | 98 |
| 2 | 52 | 97 |
| 3 | 40 | 96 |
| 4 | 35 | 96 |
| 5 | 31 | 95 |

The results show unambiguously that the content of active t-PA in an untreated cell culture supernatant diminishes by almost 70 per cent, i.e. that the specific activity of the subsequently isolated protein is only about 30 per cent of the specific activity at the time of harvest.

However, the decrease in activity of the cell culture supernatant treated according to the invention is only 5 per cent, so that addition of arginine and lysine makes it possible for cell culture supernatants to be stored temporarily without considerable loss of activity.

EXAMPLE 2

A t-PA-containing solution was dialyzed against 1.6 mol/l KSCN in 0.05 mol/l tris-HCl, pH 7.0, and then against 0.1 mol/l arginine and 0.1 mol/l lysine in 0.05 mol/l tris-HCl, pH 7.0, and was concentrated to 0.1, 0.2, 0.5, 1.0, 10, 20, 40, 60 and 80 mg of t-PA/ml. It was observed that it was possible to keep t-PA in solution up to a concentration of 60 mg/ml. The solubility limit with Tween 80(®) (0.1%) without other additives was 0.5 mg of t-PA/ml.

EXAMPLE 3

A t-PA-containing solution was dialyzed against 1.6 mol/l KSCN in 0.05 mol/l tris, pH 7.0, and then against a buffer containing 0.05 mol/l glycine, pH 7.0, together with increasing concentrations of arginine and lysine. 0.5 or 1 g/ml sucrose was added to the t-PA-containing solution where indicated. The pH of the solutions was adjusted to 7. The solutions were heated at 60° C. for 10 h. The t-PA activity was determined before and after pasteurization.

| Concentration of arginine + lysine (mol/l) | | Activity after pasteurization (%) Sucrose concentration (g/ml) | | |
|---|---|---|---|---|
| | | 0 | 0.5 | 1 |
| — | — | 0.5 | — | 68 |
| 0.001 | 0.001 | 56.0 | — | — |
| 0.05 | 0.05 | 56.9 | — | — |
| 0.1 | 0.1 | 71.3 | 88.0 | 88.0 |
| 0.2 | 0.2 | 76.1 | — | — |
| 0.5 | 0.5 | 80.7 | 91.0 | 96.3 |
| 1.0 | 1.0 | 85.6 | — | — |

The table shows that both sucrose and the addition of arginine and lysine have a stabilizing effect on plasminogen activator. Whereas the activity in a sample to which neither sucrose nor arginine or lysine has been added is almost completely destroyed by pasteurization, after addition merely of one gram of sucrose/ml 68 per cent of the initial activity is retained. This figure can be considerably improved by addition of arginine and lysine, so that 96 per cent of the initial activity is retained with a combination of 1 g/ml sucrose and of arginine and lysine, 0.5 mol/l each, which means that the loss of activity due to pasteurization becomes negligibly small.

We claim:

1. A process for the preparation of a protein solution having tissue plasminogen activator (t-PA) activity, comprising preparing a solution containing t-PA in the one- or two-chain form, or a solution containing a derivative of said t-PA which occurs naturally or which has been prepared by synthesis or genetic manipulation; and adding to said solution 0.001 to 1 mol/l of arginine and 0.001 to 1 mol/l of lysine.

2. The process as claimed in claim 18, wherein said solution containing t-PA further comprises pro-urokinase or urokinase.

3. The process as claimed in claim 1, wherein said addition step comprises dialyzing said solution containing t-PA against a buffered solution containing arginine and lysine.

4. The process as claimed in claim 1, wherein said solution containing t-PA is the supernatant of a cell culture.

5. The process as claimed in claim 1, further comprising, after the addition step, pasteurizing the solution by incubation at 40° C. to 90° C. for one to 60 hours at pH b 5 to 10.

6. The process as claimed in claim 5, further comprising, after adding the lysine and arginine and before the pasteurization step, adding an effective amount of a pasteurization stabilizing substance selected from the group consisting of sucrose and sorbitol.

7. A protein solution having t-PA activity prepared by the process as claimed in claim 1, said protein solution having a specific activity concentration of more than $5 \times 10^6$ IU/ml.

8. The process as claimed in claim 1, wherein 0.01 to 0.5 mol/l of arginine and lysine are added.

9. The process as claimed in claim 5, wherein said pasteurization is carried out at pH 6 to 8 by incubation at 50° C. to 70° C. for 6 to 16 hours.

10. The process as claimed in claim 6, wherein said stabilizing substance comprises 0.2 to 2 kg/l of sucrose, sorbitol, or any combination thereof.

11. The process as claimed in claim 3, wherein said buffer solution contains 0.1 mol/l arginine and 0.1 mol/l lysine, and has a pH of 7.

12. A process for initiating fibrinolysis in humans or animals comprising administering to a patient in need thereof an effective amount of the protein solution as claimed in claim 7.

13. The process as claimed in claim 12 wherein administration of the protein solution is effected parenterally.

* * * * *

UNITED STATES PATENT AND TRADEMARK OFFICE
CERTIFICATE OF CORRECTION

PATENT NO. : 5,068,106

DATED : November 26, 1991

INVENTOR(S) : Eric P. Paques Hans-Arnold Stohr

It is certified that error appears in the above-identified patent and that said Letters Patent is hereby corrected as shown below:

Title page, after [73] Assignee:, change "Marburg," to --Marburg/Lahn,--.

In claim 2, line 1, "18" should read --1--; and

In claim 5, line 4, delete "b".

Signed and Sealed this

Twenty-ninth Day of June, 1993

Attest:

MICHAEL K. KIRK

Attesting Officer   Acting Commissioner of Patents and Trademarks